US00PP24116P3

(12) United States Plant Patent
Wu et al.

(10) Patent No.: US PP24,116 P3
(45) Date of Patent: Dec. 24, 2013

(54) 'NORTHBRIDGE TURF BERMUDAGRASS'

(50) Latin Name: ***Cynodon transvaalensis* Burtt-Davy** *xc. dactylon* (L.) Pers.
Varietal Denomination: Northbridge Turf Bermudagrass

(75) Inventors: Yanqi Wu, Stillwater, OK (US); Dennis Loren Martin, Stillwater, OK (US); Charles M. Taliaferro, Stillwater, OK (US); Jeffrey A. Anderson, Stillwater, OK (US); Justin Q. Moss, Perkins, OK (US)

(73) Assignee: The Board of Regents For Oklahoma State University, Stillwater, OK (US)

( * ) Notice: Subject to any disclaimer, the term of this patent is extended or adjusted under 35 U.S.C. 154(b) by 15 days.

(21) Appl. No.: 13/317,968

(22) Filed: Oct. 31, 2011

(65) Prior Publication Data

US 2012/0304350 P1 Nov. 29, 2012

Related U.S. Application Data

(60) Provisional application No. 61/456,133, filed on Nov. 1, 2010.

(51) Int. Cl.
*A01H 5/00* (2006.01)

(52) U.S. Cl.
USPC ..... Plt./389

(58) Field of Classification Search
USPC ..... Plt./389
See application file for complete search history.

(56) References Cited

PUBLICATIONS

Wu et al. Turfgrass and Environmental Research Online. vol. 8, No. 16, Aug. 15, 2009.*
"Australian Patent Office PCT International Search Report, International Application PCT/US2011/001843", Dec. 12, 2011.
"Australian Patent Office PCT Written Opinion of the ISA, International Application PCT/US2011/001843", Dec. 12, 2011.
Wu, et al., "Genetic Diversity of *Cynodon transvaalensis* Burtt-Davy and Its Relatedness to Hexaploid C. *dactylon* (L.) Pers. as Indicated by AFLP Markers", Mar. 25, 2005, pp. 848-853, vol. 45.
Wu, et al., "Turfgrass and Environmental Research Online", Aug. 15, 2009, vol. 8, No. 16, Published in: US.

* cited by examiner

*Primary Examiner* — Annette Para
(74) *Attorney, Agent, or Firm* — Fellers, Snider, Blankenship, Bailey & Tippens, P.C.

(57) ABSTRACT

'Northbridge Turf Bermudagrass' is a clonally propagated FI hybrid from a cross of *C. transvaalensis* OSU selection '2747' (2n=2x=18) by *C. dactylon* var. *dactylon* OSU selection '3200E 4-1'.

6 Drawing Sheets

CROSS REFERENCE TO RELATED APPLICATIONS

This application claims the priority of U.S. Provisional Patent Application No. 61/456,133 entitled "TURF BERMUDAGRASS," filed Nov. 1, 2010, the contents of which are hereby incorporated by reference.

SUMMARY OF THE INVENTION

A new turf bermudagrass cultivar, 'Northbridge', is provided. Designated "Bermudagrass, *Cynodon transvaalensis* Burtt-Davy xc. *dactylon* (L.) Pers.", the 'Northbridge Turf Bermudagrass' cultivar is also referred to herein by its experimental designation 'OKC 1134'.

DETAILED BOTANICAL DESCRIPTION

Description, Origin, and History

Figure 1:
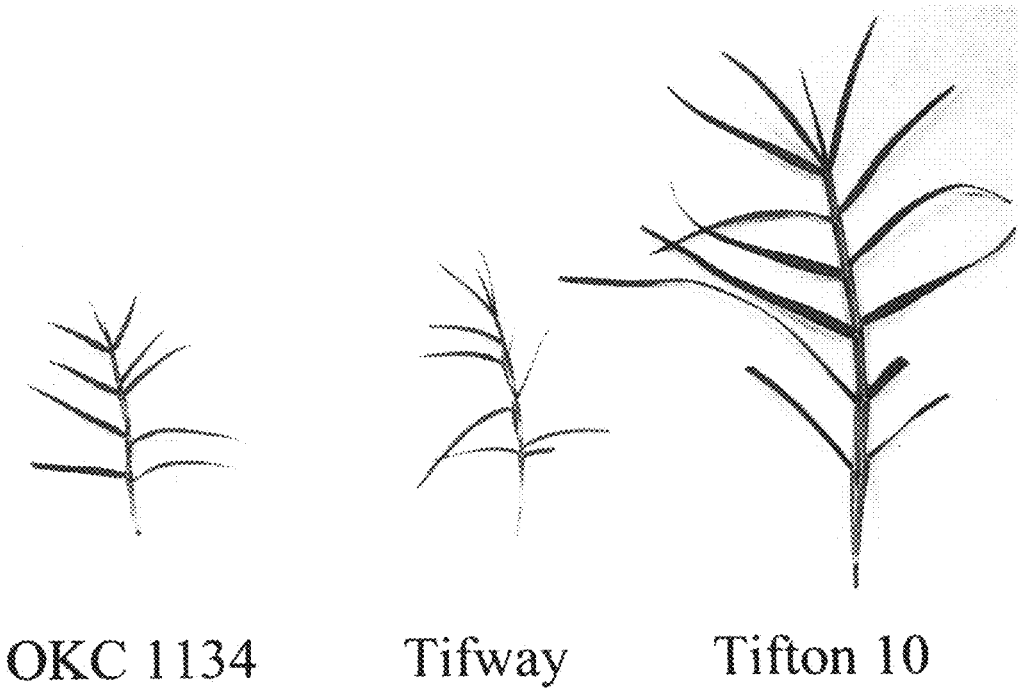
FIG. 1 is a comparison of 'Northbridge Turf Bermudagrass' (denoted as 'OKC 1134') to Tifway and Tifton 10.
Figure 2:
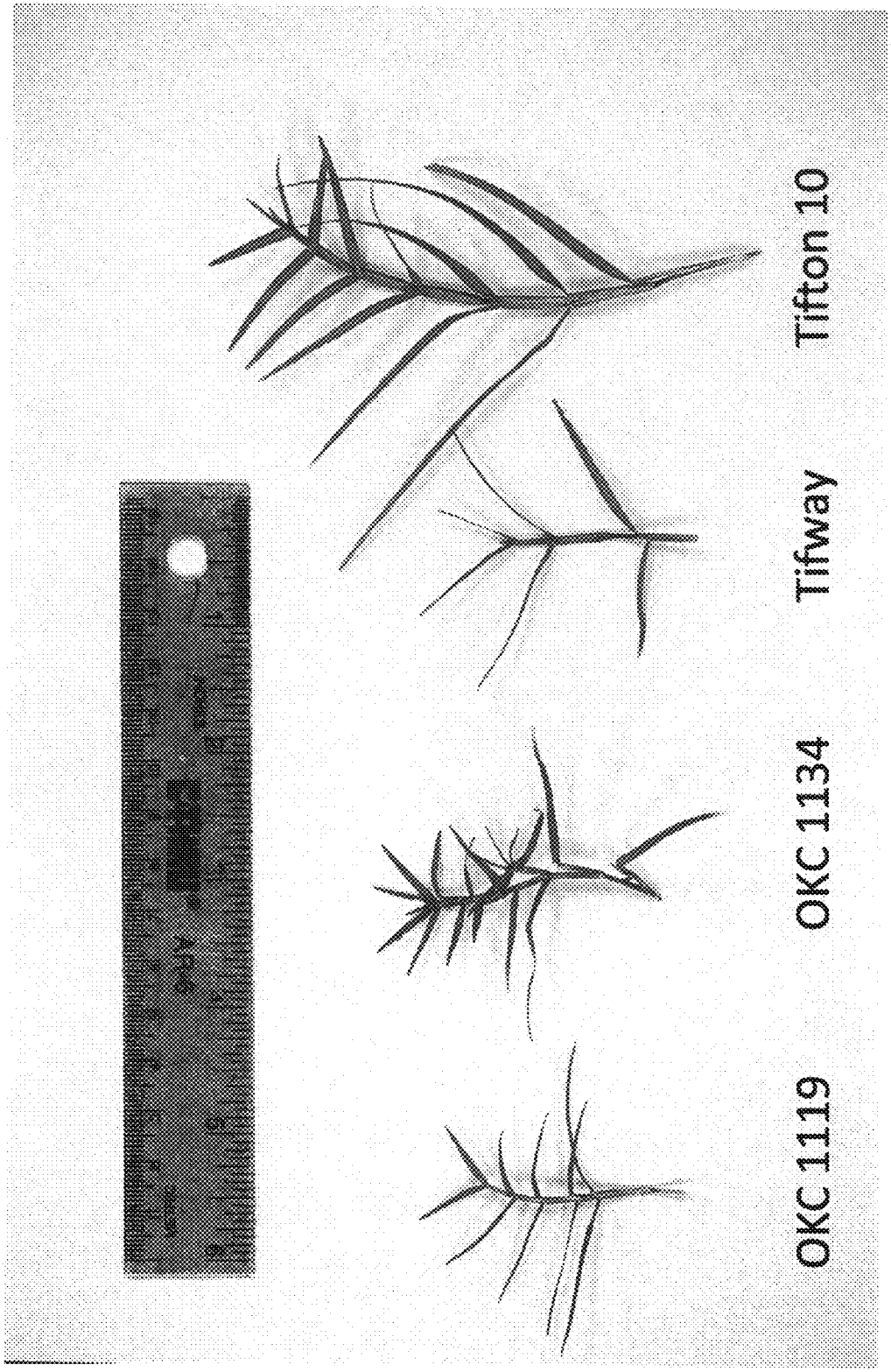
FIG. 2 is a comparison of 'Northbridge Turf Bermudagrass' (denoted as 'OKC 1134') to OKC 1119, Tifway and Tifton 10.
Figure 3:
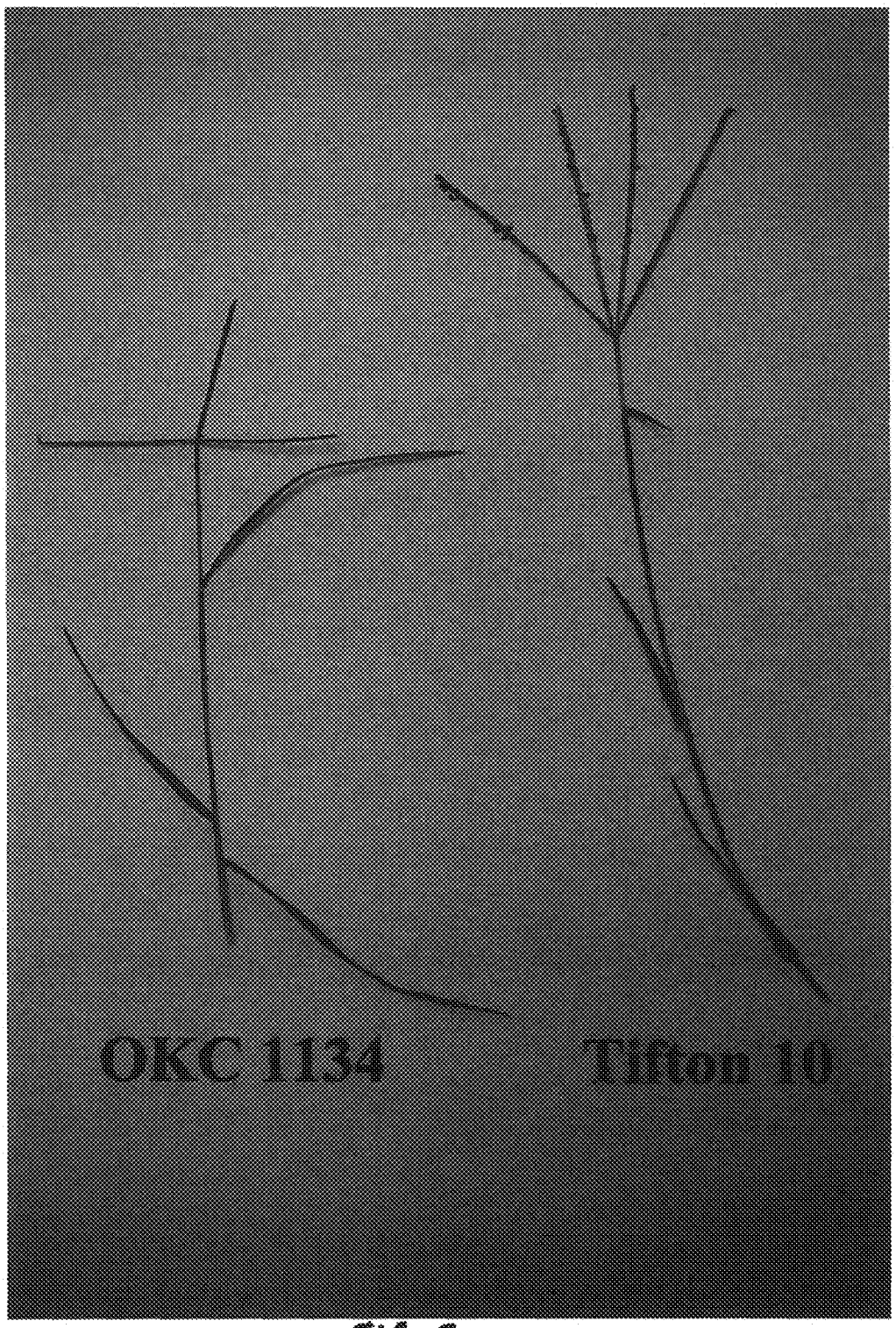
FIG. 3 is a photo of the inflorescense of 'Northbridge Turf Bermudagrass' (denoted as 'OKC 1134') and Tifton 10.

'Northbridge Turf Bermudagrass' is a clonally propagated FI hybrid from a cross of *C. transvaalensis* Oklahoma State University ("OSU") selection '2747' (2n=2x=18) by *C. dactylon* var. *dactylon* OSU selection '3200E 4-1'. Both the *C. transvaalensis* and *C. dactylon* plants were selected from broad genetic base populations for use as parents in interspecific crosses. Crossing between 2747 and 3200E 4-1 was achieved by planting clonal plants of each in close proximity in isolation from other bermudagrass plants. Seed was harvested from plants of the respective species in 1998 and used to start 630 space-planted plants in a screening nursery in spring 1999 on the Agronomy Research Station, Stillwater, Okla.

In spring 2001, 118 plants from the screening nursery were advanced to a replicated screening test (Test 2001-1) on the Agronomy Research Station. During summer 2004, 'Northbridge Turf Bermudagrass' along with other selected plants from Test 2001-1, were included in a replicated mowing test on the OSU Turf Research Center, Stillwater, Okla. Entries in this test were maintained under a golf course fairway management regime and evaluated for turf quality and other traits influencing performance (Han, 2009). Based on performance in this test, 'Northbridge Turf Bermudagrass' was entered in the 1997 National Turfgrass Evaluation Program (NTEP) bermudagrass test.

'Northbridge Turf Bermudagrass' is presumed to have 2n=3x=27 chromosomes. The variety is sterile and must be vegetatively propagated. OSU SSR molecular marker DNA profiling experiments definitely indicated 'Northbridge Turf Bermudagrass' is a unique genotype, distinct from other commercial cultivars, and other two OSU vegetatively propagated turf bermudagrass clones OKC 1119 and OKC 70-18 (Wang et al., 2010).

Characteristics and Performance

'Northbridge Turf Bermudagrass' has been evaluated in several OSU experiments, and more extensively in the 2007 NTEP test. Data from the NTEP test were collected from 8 locations in 2007, 16 locations in 2008, and 19 locations in 2009 (see 2007 Progress Report NTEP No. 09-2; 2008 Progress Report NTEP No. 09-1; 2009 Progress Report NTEP No. 10-4, each incorporated herein by reference as it is set out in its entirety, available at: http://www.ntep.org/bg.htm). The major performance characteristics of 'Northbridge Turf Bermudagrass' are described as follows:

'Northbridge Turf Bermudagrass' is highly infertile, producing only very few seed when grown in the presence of an effective pollinator. Consequently, it must be propagated asexually. Chromosome number has not yet been determined. It is likely a tetraploid with 2n=4x=36 chromosomes.

For mature plants grown in a greenhouse, leaf blade length and leaf blade width of 'Northbridge Turf Bermudagrass' was similar to that of Tifway, and much smaller relative to Tifton 10 (Table 1). 'Northbridge Turf Bermudagrass' had shorter internode length relative to Tifway and Tifton 10. Internode diameter of 'Northbridge Turf Bermudagrass' bermudagrass was larger than that of Tifway, but smaller than that of Tifton 10.

For plants grown in fields at Stillwater and Perkins, Okla. (Table 2), leaf blade width of OKC 1134 was similar to Tifway, but much narrower than Tifton 10. Leaf blades of 'Northbridge Turf Bermudagrass' were longer relative to those of Tifway and Tifton 10. Internode length of 'Northbridge Turf Bermudagrass' was similar to that of Tifway, but longer than that of Tifton 10. 'Northbridge Turf Bermudagrass' had smaller internode diameter than Tifton 10, but wider than Tifway (Table 2).

TABLE 1

Table 1. Measurements of leave blades and internodes of potted plants of 'Oklahoma Turf Bermudagrass', Tifway and Tifton 10 bermudagrasses, grown in a greenhouse at the Agronomy Research Station, Oklahoma State University. Data were collected in 2010 from three replications each having 10 sub-samples for each cultivar.

| Measured traits | NorthBridge | Tifway | Tifton 10 | 5% LSD |
|---|---|---|---|---|
| $4^{th}$ leaf blade length (cm)* | 2.13 | 1.97 | 2.80 | 0.33 |
| $4^{th}$ leaf blade width (mm) | 1.84 | 1.83 | 2.72 | 0.12 |
| $2^{nd}$ internode length (cm) | 0.80 | 1.12 | 1.09 | 0.15 |
| $2^{nd}$ internode diameter (mm) | 0.68 | 0.56 | 1.01 | 0.07 |

*Leaf from shoot apex.

TABLE 2

Table 2. Measurements of leave blades and internodes of field-grown plants of 'Northbridge Turf Bermudagrass', Tifway and Tifton 10 bermudagrasses. The field plots were established in 2010 and data were collected in 2011. Data of three replications each having 10 subsamples were collected for each cultivar.

| Location | Measured traits | NorthBridge | Tifway | Tifton 10 | 5% LSD |
|---|---|---|---|---|---|
| Agronomy Research Farm, Stillwater, OK | $4^{th}$ leaf blade length (cm) | 7.15 | 4.42 | 3.39 | 0.43 |
| | $4^{th}$ leaf blade width (mm) | 1.70 | 1.73 | 2.80 | 0.15 |
| | $2^{nd}$ internode length (cm) | 1.51 | 1.61 | 0.69 | 0.22 |
| | $2^{nd}$ internode diameter (mm) | 0.54 | 0.47 | 1.02 | 0.07 |
| Cimarron Valley Research Station, Perkins, OK | $4^{th}$ leaf blade length (cm) | 6.45 | 3.94 | 3.07 | 0.48 |
| | $4^{th}$ leaf blade width (mm) | 1.66 | 1.78 | 2.64 | 0.16 |
| | $2^{nd}$ internode length (cm) | 1.20 | 1.02 | 0.63 | 0.17 |
| | $2^{nd}$ internode diameter (mm) | 0.67 | 0.54 | 1.14 | 0.08 |

'Northbridge Turf Bermudagrass' DNA profiles are different from those of 30 commercial clonal bermudagrass cultivars and one experimental genotype as revealed by 11 simple sequence repeat (SSR) markers (FIG. 1) (Wang et al., 2010).

Figure 4:
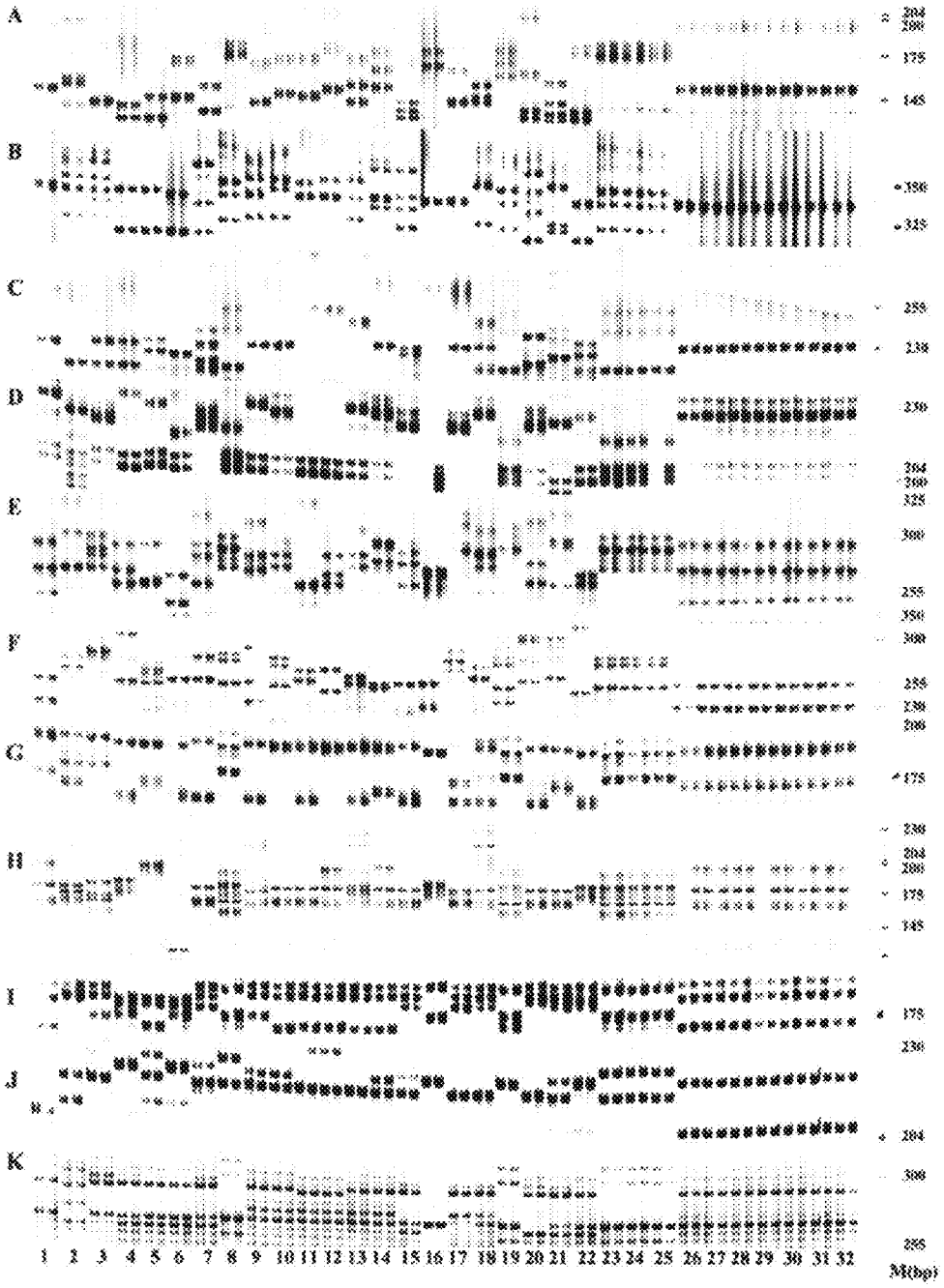
FIG. 4 is an illustration of the DNA profiles of various turf bermudagrass cultivars including 'Northbridge Turf Bermudagrass' (denoted as 'OKC 1134').
Figure 5:
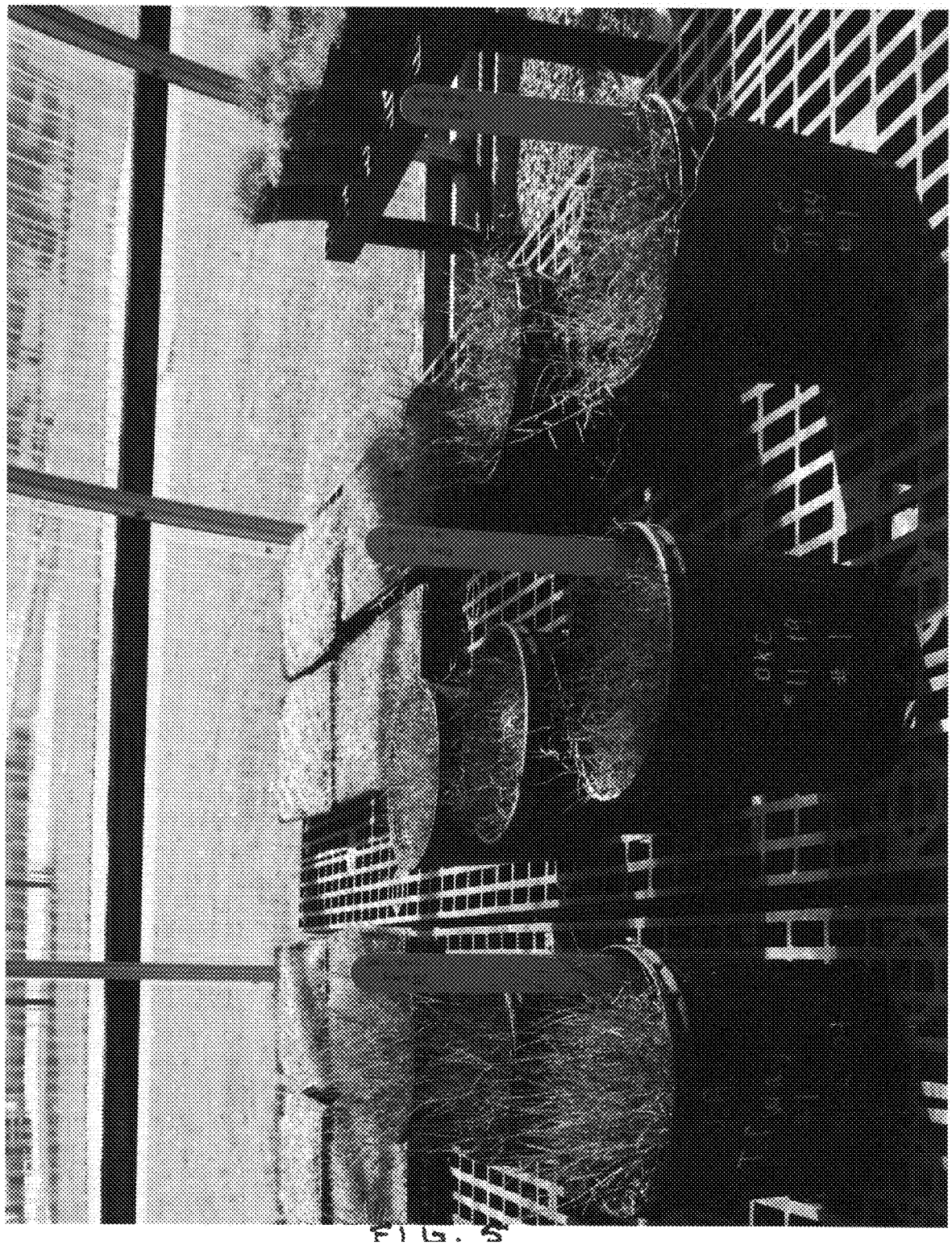
FIG. 5 is a comparison of 'Northbridge Turf Bermudagrass' (denoted as 'OKC 1134') to OKC 1119 and Tifway growing in a greenhouse.
Figure 6:
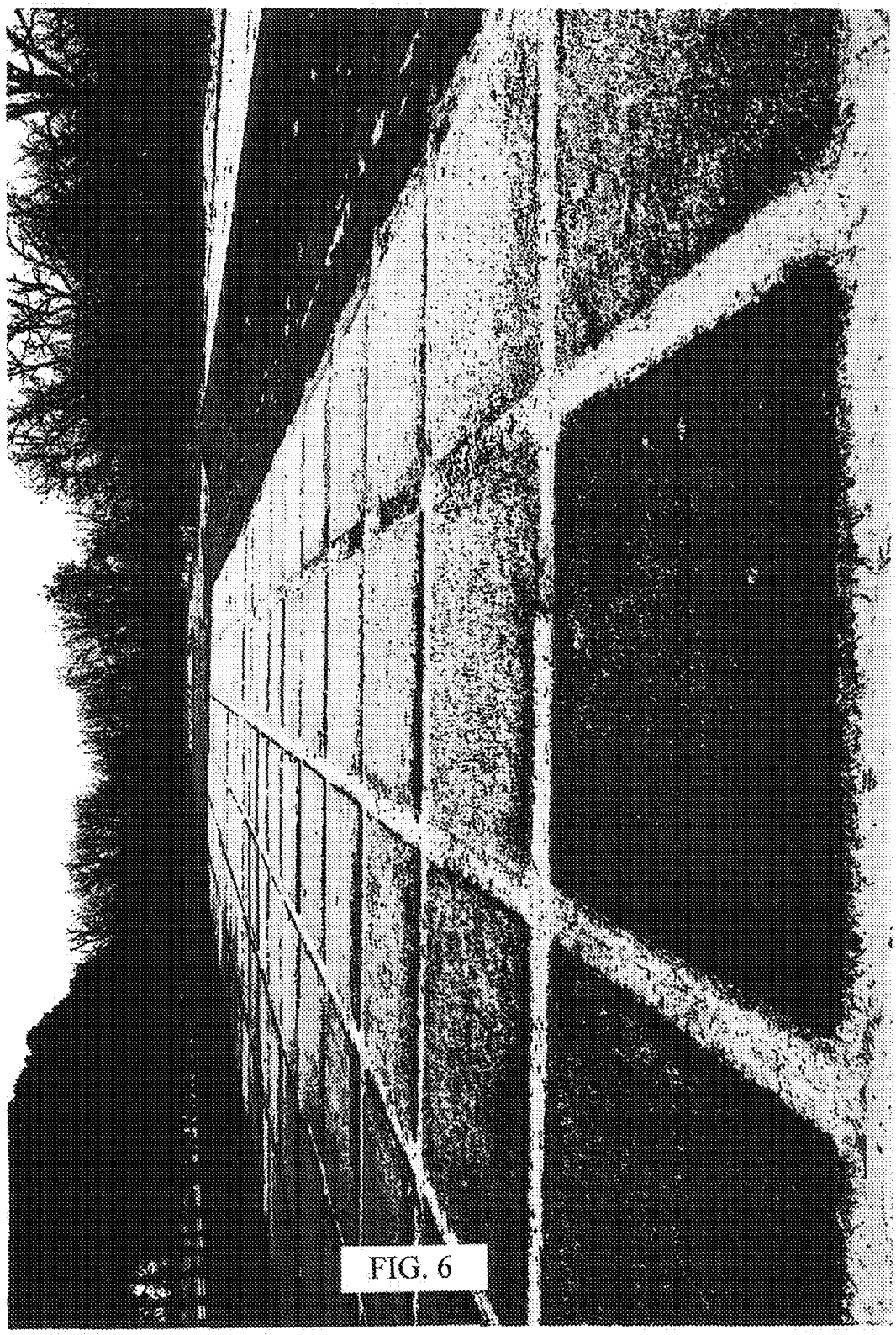
FIG. 6 is a photo of 'Northbridge Turf Bermudagrass' (denoted as 'OKC 1134') growing outdoors.

FIG. 4 illustrates DNA profiles of 32 vegetative turf bermudagrass cultivars amplified with 11 SSR primer pairs (PPs). The numbers at the bottom of the gel images: 1=Baby, 2=Celebration, 3=FloraTex, 4=Midfield, 5=Midlawn, 6=Midway, 7=MS-Choice, 8=MS-Price, 9=MS-Express, 10=OKC 70-18, 11=Latitude 36 (OKC 1119), 12='Northbridge Turf Bermudagrass', 13=Patriot, 14=Premier, 15=Quickstand, 16=Sunturf, 17=Texturf 10, 18=Tifton 10, 19=TifGrand, 20=U-3-SIU, 21=Vamont, 22=Midiron, 23=TifSport, 24=Tifway, 25=Tifway II, 26=TifEagle, 27=Tifgreen, 28=Champion, 29=FloraDwarf, 30=Mini Verde, 31=MS-Supreme, 32=TifDwarf. Image A (labeled on the left side) was generated by SSR PP CDCA31-32, B by CDCA55-56, C by CDCA77-78, D by CDCA133-134, E by CDCA155-156, F by CDCA379-380, G by CDCA747-748, H by CDE89-90, I by CDE127-128, J by CDE215-216, and K by CDE375-376 (Wang et al., 2010. Use of the figure was permitted from the journal *Crop Science*).

Turf quality: The turf quality of 'Northbridge Turf Bermudagrass' is very high as indicated by ratings collected in 2008 and 2009 from the 2007 NTEP test. In this test, the turf quality of 'Northbridge Turf Bermudagrass' has been statistically equal to that of Tifway and Premier. These three varieties along with another OSU entry (OKC 1119), have had the highest quality ratings of all 31 entries at most locations (2008 NTEP Tables 1A&C, 2A&C, 3A&C, & 4A&C; 2009 NTEP Tables 1A&C, 2A&C, 3A&C, & 4A&C). The high turf quality of 'Northbridge Turf Bermudagrass' as indicated by NTEP data is supported by data from internal OSU testing indicating it to have turf quality equal to or better than other current industry standard bermudagrass varieties:

Cold tolerance and spring greenup: Freeze tolerance evaluations at OSU provided $T_{mid}$ COC, cultivars followed by the same letter are not significantly different in freeze tolerance at P:S 0.05) values for 'Northbridge Turf Bermudagrass' (-8.9a), Midlawn (-8.3a), Tifway (-7.5b). The results indicated 'Northbridge Turf Bermudagrass' has a level of freeze tolerance on a par with that of Midlawn and superior to Tifway. Midlawn has been widely known as one of the most cold hardy turf bermudagrass varieties. The spring greenup rating (6.4) of 'Northbridge Turf Bermudagrass' was statistically better than that of Tifway (5.7), Premier (6.0), and Midlawn (4.3) in 2009 while spring greenup rating (5.7) of 'Northbridge Turf Bermudagrass' was equal to that of Tifway (5.5), Premier (5.3), and Midlawn (5.3) in 2008 (2008 NTEP Table 8C and 2009 NTEP Table 10C). The level of winter hardiness of 'Northbridge Turf Bermudagrass' should allow it to be used in the transition zone environment with reduced risk of freeze injury relative to Tifway.

Genetic color: 'Northbridge Turf Bermudagrass' was rated statistically equal to Tifway and Premier, and superior to Midlawn in genetic color in 2008 (2008 NTEP Table 7C). 'Northbridge Turf Bermudagrass' had lighter green color than 'Patriot' bermudagrass in both 2008 and 2009, and Tifway and Premier in 2009 (2008 NTEP Table 7C; 2009 NTEP Table 9C). 'Northbridge Turf Bermudagrass' grown in the field with 100 lb N/ac applied in the summer had leaves of strong yellowish green color, rated as RHS143C, similar to Tifway, but less dark than Tifton 10, which was rated as RHS 144A. The leaf color was visually rated based on the color systems of Azalea Society of America (http://www.azaleas.org/index.pl/rhsmacfan3.html).

Leaf texture: 'Northbridge Turf Bermudagrass' has fine leaf texture similar to Tifway and Premier, but finer than Midlawn (2008 NTEP Table 9C and 2009 NTEP Table 11 C). Its stem diameter is about the same as Tifway and Premier.

Sod tensile strength: Field evaluations at OSU indicated different sod tensile strength values (kg/dm$^2$) for 'Northbridge Turf Bermudagrass' (186.2 in 2004 and 175.1 in 2005) and for Tifway (161.3 in 2004 and 143.7 in 2005), and the differences are statistically significant only in 2005 (Han, 2009). Tifway has exhibited high sod tensile strength in both controlled experiments and sod production.

Sod density: Ratings in spring, summer and fall in multiple locations over both 2008 and 2009 indicated sod density of 'Northbridge Turf Bermudagrass' to be slightly higher than, or about equal to, that of Tifway and Premier, and significantly higher than that of Midlawn (2008 NTEP Tables 10C, 11C, 12C; 2009 NTEP Tables 12C, 13C & 14C).

Seedhead ratings: In 2008, 'Northbridge Turf Bermudagrass' had seedhead ratings better than or equal to Tifway, Premier and Midlawn in most locations, but produced more seedheads than Midlawn and Tifway in TX2 (2008 NTEP Tables 21 Co 22C, 23C &24C). In 2009, 'Northbridge Turf Bermudagrass' had seedhead ratings better than or equal to Tifway, Premier and Midlawn at all locations (2009 NTEP Tables 24C, 28C, 29C, 30C & 31C).

Disease response: 'Northbridge Turf Bermudagrass' has demonstrated a high level of resistance to Large Patch disease (2009 NTEP 27C).

Insect response: No significant insect problems have been observed for 'Northbridge Turf Bermudagrass' except in FL 1, where mole cricket resistance rating of 'Northbridge Turf Bermudagrass' as numerically lower than that of Tifway, Midlawn and Premier although the differences are not statistically significant (2009 NTEP Table 26C).

Salinity response: Grown under saline stress at Las Cruces, N. Mex., 'Northbridge Turf Bermudagrass' has demonstrated a high level of salinity tolerance, better than Midlawn, Premier and Tifway in 2008, better than Midlawn and Premier and equal to Tifway in 2009 (2008 NTEP Table 6C, 2009 NTEP Table 8C).

Traffic tolerance: Traffic tolerance ratings of 'Northbridge Turf Bermudagrass' were equal to that of Tifway and Premier, and better than that of Midlawn in AR2 and FL2 (2009 NTEP Tables 5C, 6C). 'Northbridge Turf Bermudagrass' had traffic tolerance about equal to Tifway, Premier and Midlawn in NC 1 (2009 NTEP Table 7C). 'Northbridge Turf Bermudagrass' was lower in traffic tolerance than Tifway and equal to Premier and Midlawn in FL2 (2008 NTEP Table 5C).

Herbicide tolerance: OSU field experiments indicated the effects of various post emergence herbicides on the establishment rate of 'Northbridge Turf Bermudagrass' compared to OKC 1119, OKC 7018 and Tifway (Koh et al., 2010). Herbicide treatments were as follows: 1) Untreated control, 2) MSMA at 2.2 kg ai/ha, 3) MSMA at 4.4 kg ailha, 4) Quinclorac at 0.8 kg ae/ha, 5) Quinclorac at 1.6 kg ae/ha, 6) Metsulfuron at 0.025 kg ailha, and 7) Metsulfuron at 0.050 kg ailha. There was no negative effect on 'Northbridge Turf Bermudagrass' establishment rate when treated with the labeled rates of the herbicides. In addition, 'Northbridge Turf Bermudagrass' performed equal to Tifway and OKC 1119 and greater than OKC 7018 in herbicide tolerance ratings and reached 100% establishment at 8 weeks after planting.

Establishment: 'Northbridge Turf Bermudagrass' has a better or equal establishment rate compared with Tifway, Premier and Midlawn. Establishment ratings of 'Northbridge Turf Bermudagrass' were higher than that of Tifway, Premier and Midlawn in LAI (2007 NTEP Table 18C), higher than Midlawn and Tifway, and equal to that of Premier in NC2 (2007 NTEP Table 20C), better than Tifway, and equal to Premier and Midlawn in TX2 (2007 NTEP Table 23C) equal to that of Premier, Tifway and Midlawn in AZ1, MS2, OKI, TN2 (2007 NTEP Tables 17C, 19C, 21C, 22C). 'Northbridge Turf Bermudagrass' had an establishment rating slightly lower than Premier and Tifway, but quicker than Midlawn in FL2 (2008 NTEP Table 28C), and equal to Premier, Tifway and Midlawn in FL3 (2008 NTEP Table 29C).

Summary comparative performance: The major strengths of 'Northbridge Turf Bermudagrass' are its high turf quality, fine texture, improved winter hardiness, early greenup, high sod density, and very high sod tensile strength. The combined performance data indicate it has less risk of winter injury than Tifway, perhaps Premier, while providing equal turf quality. Compared to Midlawn, its turf quality is much improved. 'Northbridge Turf Bermudagrass' is much better than Midlawn in sod tensile strength, a major consideration for sod growers.

We claim:

1. A turf bermudagrass plant substantially as described and illustrated in the specification herein.

* * * * *